United States Patent
Alsuhaibani

(10) Patent No.: US 11,565,050 B2
(45) Date of Patent: Jan. 31, 2023

(54) ADAPTER FOR SINGLE-HANDED OPERATION OF SYRINGE DURING ASPIRATION OPERATION

(71) Applicant: ALSAHAB MEDICAL COMPANY, Riyadh (SA)

(72) Inventor: Abdulaziz A Alsuhaibani, Riyadh (SA)

(73) Assignee: ALSAHAB MEDICAL COMPANY, Riyadh (SA)

( * ) Notice: Subject to any disclaimer, the term of this patent is extended or adjusted under 35 U.S.C. 154(b) by 590 days.

(21) Appl. No.: 16/566,880

(22) Filed: Sep. 11, 2019

(65) Prior Publication Data
US 2021/0038820 A1    Feb. 11, 2021

(30) Foreign Application Priority Data

Aug. 6, 2019 (SA) .................................. 19400915

(51) Int. Cl.
*A61M 5/31* (2006.01)
(52) U.S. Cl.
CPC ....... *A61M 5/3148* (2013.01); *A61M 2205/19* (2013.01); *A61M 2205/586* (2013.01)
(58) Field of Classification Search
CPC ............ A61M 5/3148; A61M 2205/19; A61M 2205/586
See application file for complete search history.

(56) References Cited

U.S. PATENT DOCUMENTS

| 1,221,103 | A | * | 4/1917 | Sorensen | ................ | A61M 1/80 |
| | | | | | | 604/314 |
| 3,325,061 | A | * | 6/1967 | Ellsworth | ........... | A61M 5/3137 |
| | | | | | | D24/114 |
| 3,819,091 | A | * | 6/1974 | Hollender | ............. | A61M 5/315 |
| | | | | | | 222/327 |
| 3,990,446 | A | * | 11/1976 | Taylor | ................ | A61M 5/3137 |
| | | | | | | 604/227 |

(Continued)

FOREIGN PATENT DOCUMENTS

| AU | 2003203054 A1 | * 9/2003 | ......... A61B 10/0283 |
| DE | 20 2012 006 191 U1 | 8/2012 | |

(Continued)

OTHER PUBLICATIONS

International Search Report and Written Opinion of the International Searching Authority dated Jun. 29, 2020 in International Patent Application No. PCT/IB2020/051601, 11 pages.

*Primary Examiner* — Nathan R Price
*Assistant Examiner* — Mark A Igel
(74) *Attorney, Agent, or Firm* — Xsensus LLP

(57) ABSTRACT

An adapter for single-handed operation of a syringe includes a clip having a pair of arcuate legs that straddle at least half of an outer diameter of a barrel of a syringe, the clip having an upper opening. The adapter also includes an integrated structure including an extension spine that extends in an axial direction and outside of the barrel of the syringe, a forward flange disposed at a first end of the extension spine and having arcuate legs that straddle at least half of the outer (Continued)

diameter of the barrel of the syringe, and a support that that is disposed on an opposite end of the extension spine and is positioned adjacent to a thumb press of a plunger rod of the syringe.

23 Claims, 8 Drawing Sheets

(56) References Cited

U.S. PATENT DOCUMENTS

| | | | | |
|---|---|---|---|---|
| 4,484,915 A * | 11/1984 | Tartaglia | ............ | A61B 10/0045 604/227 |
| 4,639,248 A * | 1/1987 | Schweblin | ............ | B01L 3/0217 604/218 |
| 4,813,433 A | 3/1989 | Downey | | |
| 5,115,816 A * | 5/1992 | Lee | ...................... | A61M 5/1782 D24/146 |
| 5,135,511 A * | 8/1992 | Houghton | ............ | A61M 5/3148 604/233 |
| 5,582,595 A * | 12/1996 | Haber | ................... | A61M 5/315 604/218 |
| 5,814,023 A * | 9/1998 | Fulk | ................. | A61B 5/150992 604/232 |
| 5,833,668 A * | 11/1998 | Aguilar | ............... | A61M 5/3135 604/227 |
| 6,231,550 B1 * | 5/2001 | Laughlin | ............. | A61M 5/3148 604/187 |
| 2004/0073172 A1 * | 4/2004 | Acha Gandarias | . | A61M 3/0262 604/218 |
| 2005/0192543 A1 * | 9/2005 | Sibbitt | ............... | A61M 5/31511 604/218 |
| 2005/0215956 A1 * | 9/2005 | Nerney | .................. | A61M 5/315 604/218 |
| 2005/0215958 A1 * | 9/2005 | Hawthorne | ........ | A61B 5/15003 604/227 |
| 2006/0258990 A1 * | 11/2006 | Weber | ..................... | A61M 5/20 604/208 |
| 2011/0046604 A1 * | 2/2011 | Felsovalyi | .............. | A61M 5/19 604/218 |
| 2013/0131606 A1 * | 5/2013 | Bertocci | .......... | A61M 5/31515 604/227 |
| 2019/0381252 A1 * | 12/2019 | Joseph | ................ | A61M 5/3137 |
| 2022/0001109 A1 * | 1/2022 | Simon | ................ | A61M 5/3148 |

FOREIGN PATENT DOCUMENTS

| | | | | |
|---|---|---|---|---|
| JP | 2000-296178 A | | 10/2000 | |
| JP | 2000296178 A | * | 10/2000 | ............ A61M 1/815 |
| JP | 2014-030559 A | | 2/2014 | |
| JP | 2014030559 A | * | 2/2014 | ......... A61B 10/0283 |
| WO | WO-03068073 A1 | * | 8/2003 | ......... A61B 10/0283 |
| WO | WO-2020113123 A1 | * | 6/2020 | ............ A61M 1/815 |
| WO | WO-2022047326 A1 | * | 3/2022 | ............ A61M 1/815 |

* cited by examiner

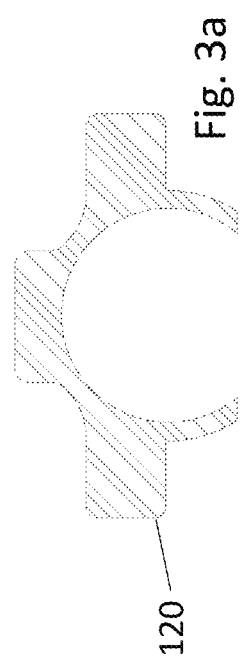
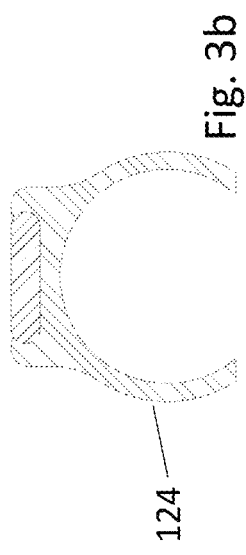
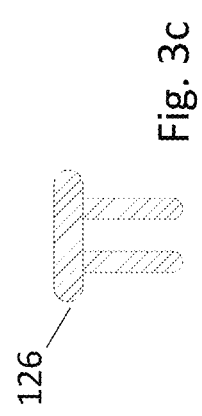

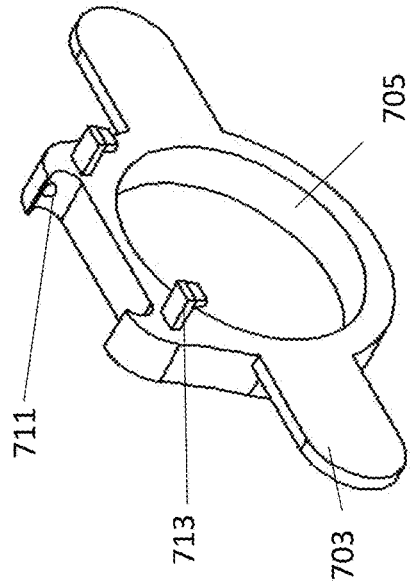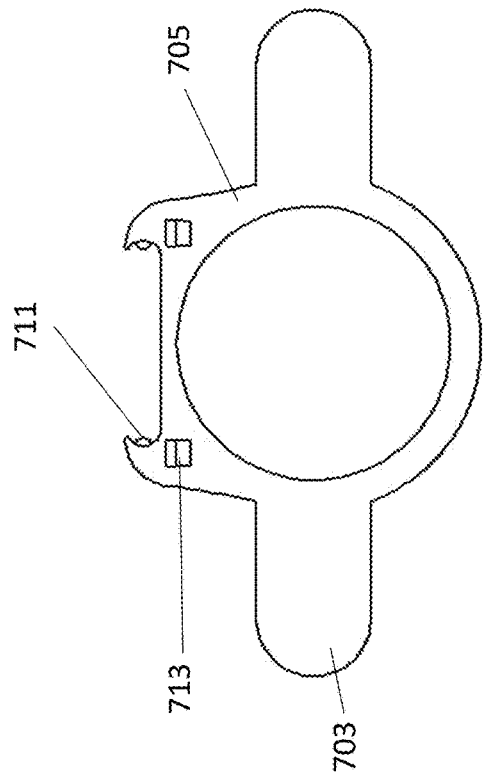

ADAPTER FOR SINGLE-HANDED OPERATION OF SYRINGE DURING ASPIRATION OPERATION

CROSS-REFERENCE TO RELATED APPLICATION

This application claims priority to Saudi Arabia Patent Application No. 119400915, filed Aug. 6, 2019, the entire contents of which are incorporated herein by reference.

BACKGROUND

Field of the Invention

The present disclosure generally relates to the field of medicine, including medical devices, as well as other fields where syringes may be used in aspiration and injection modes of operation.

Description of the Related Art

Medical syringes are used in both injection and aspiration modes. Conventionally, when a syringe is used to inject medicine (or other fluids) via a needle into a vein or the like, the operator holds the syringe in one hand and squeezes the plunger into the syringe cylinder using the thumb and fingers of the same hand. However, when a syringe is used to aspirate or withdraw blood or other fluid from a needle inserted in a vein or the like, the operator uses two hands, typically holding the cylinder in one hand while pulling the plunger out of the cylinder with the other hand.

Specialty syringes, such as that described in U.S. Pat. No. 4,484,915, have been made with multiple axially extending members that attach to a movable flange disposed at a forward end of the syringe. The flange is formed with circular opening into which a syringe body is inserted, which allows the fingers of the operator to apply a backward force (away from the forward end of the syringe) that is mechanically translated to the plunger. A fixed flange is fixedly included at the back end of the cylinder so the operator may place their thumb on the fixed flange to provide an oppositely oriented force to the force applied by the operator's fingers on the movable flange during an aspiration operation. During the aspiration operation, the movable flange is moved toward the fixed flange, and the multiple axial extending members move along an outer surface of the syringe.

SUMMARY

An adapter is described for single-handed operation of a syringe. The adapter includes a clip having a pair of arcuate legs that straddle at least half of an outer diameter of a barrel of a syringe, the clip also having an upper opening. The adapter also includes an integrated structure including an extension spine that extends in an axial direction and outside of the barrel of the syringe, a forward flange disposed at a first end of the extension spine and having arcuate legs that straddle at least half of the outer diameter of the barrel of the syringe, and a support that is disposed on an opposite end of the extension spine and is positioned adjacent to a thumb press of a plunger rod of the syringe. The adapter allows the operator to single-handedly perform an aspiration operation. However, while the adapter remains on the syringe, the operator may grasp the syringe as an operator normally does during an injection operation. A forward flange may include one or more radially extending wings, which provide one or more surfaces for the operator to apply a backward force during the aspiration operation.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 3a is a cross-sectional view of an adapter forward flange according to the first embodiment;

FIG. 3b is a cross-sectional view of an adapter clip according to the first embodiment;

FIG. 3c is a cross-sectional view of an adapter pi-support according to the first embodiment;

FIG. 8a is a perspective view of a clip according to third embodiment

FIG. 8b is a cross-sectional view of a clip according to third embodiment

DETAILED DESCRIPTION

As used herein, an element or step recited in the singular and proceeded with the word "a" or "an" should be understood as not excluding plural elements or steps, unless such exclusion is explicitly recited. Furthermore, references to "one embodiment" of the present invention are not intended to be interpreted as excluding the existence of additional embodiments that also incorporate the recited features.

The present inventor identified several suboptimal features about conventional syringes that are used for both injection and aspiration, as well as adapters that assist in aspiration. First, the inventor recognized that in conventional injection mode operator's normally clamp the barrel of the syringe between the operator's index finger and the middle finger, while depressing the plunger with the operator's thumb. However, a different gripping action is used for aspiration. Typically, aspiration is performed with two hands, one holding the body of the syringe, while the other grips the end of the plunger and withdraws the plunger from the body of the syringe. Two-handed operation is not ideal because the operator may very well want to use their other hand for another task, such as holding a bottle while withdrawing a sample. While devices such as that described above in U.S. Pat. No. 4,484,915 allow for a one-handed aspiration operation, it does so by integrating a complex three part structure with a syringe, and prevents an operator from conveniently using a single configuration for both injection and aspiration. Moreover, the multiple axial extending members move along an outer surface of the syringe which makes it difficult for the operator to position their index and middle fingers in normal positions about the syringe barrel because the multiple axial extending members can too easily rub against one, or both, of the operator's fingers. Thus, during an aspiration operation the second flange is added with the axially extending members to support a dedicated aspiration operation.

The present inventor also recognized that a universal adapter with a two piece construction would allow the operator to adapt a variety of syringes to injection/aspiration operations without need of specialized adapters having flanges that are perfectly fit around an entirety of the syringe body. Thus, the two piece design not only allows for injection and aspiration, but it does so for a variety of syringe configuration. Furthermore, using a two piece adapter, if the adapter is discarded after one or multiple uses, the amount of medical waste generated as compared with conventional devices or 3-piece adapters is reduced.

Figure 1:
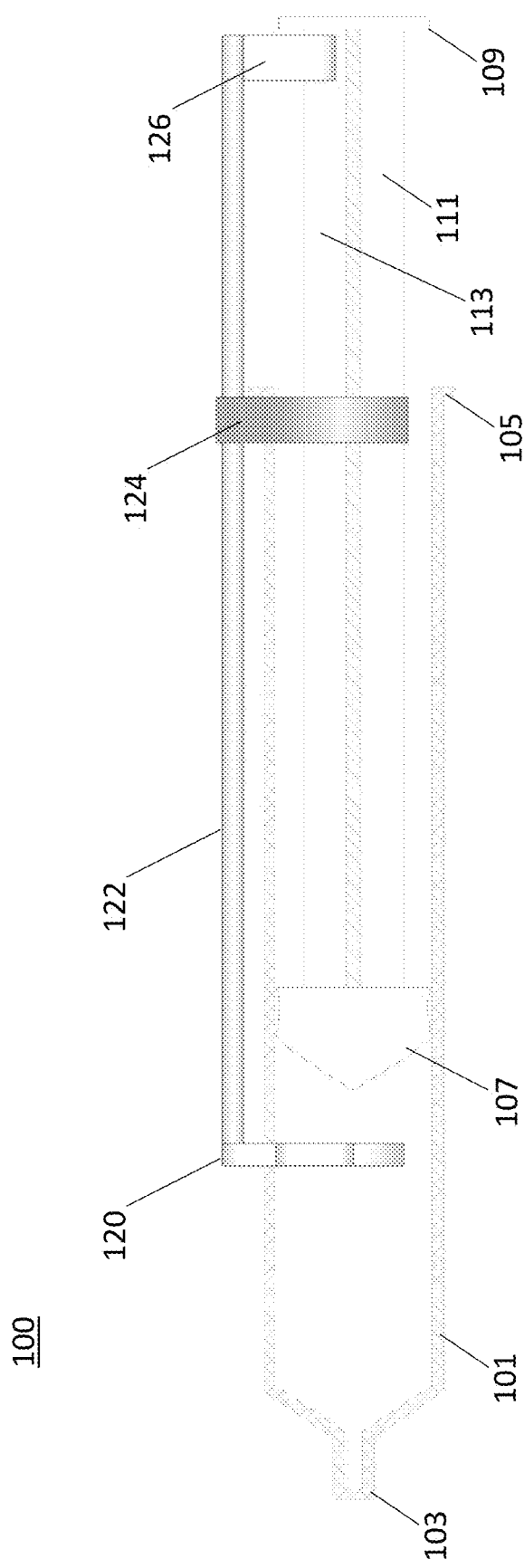
FIG. 1 is a side view of a syringe with an adapter for single-handed use of the syringe during an aspiration operation, according to a first embodiment.

Referring now to the drawings, wherein like reference numerals designate identical or corresponding parts throughout the several views, FIG. 1 illustrates a syringe with adapter for single-handed aspiration operation 100. A syringe barrel 101 has a generally cylindrical main body is hollow and tapers to a small opening at a syringe hub 103 where a needle may optionally be attached. The opposite end of the syringe barrel 101 has a wider opening having an inner circumference that matches an outer circumferences of a syringe seal 107. At the wider end of the syringe barrel 101, a syringe lip 105 is integrally formed on the outer surface of the syringe barrel 101 and it is part of barrel flange, and extends radially outward from the syringe barrel 101, and serves as a structural backing for the adapter clip 124.

The syringe seal 107 is attached to an end of a syringe plunger rod 111, and is inserted into the wider opening of the syringe barrel 101. The syringe seal 107 is made of synthetic rubber and is friction fit to the inner wall of the syringe barrel 101 so that when the syringe plunger rod 111 is pressed on the syringe plunger thumb press 109 toward the hub 103, fluid in the syringe barrel 101 between the syringe seal 107 and the hub 103 is urged toward the hub 103 and emitted through the opening in the hub 103. If a needle is affixed to the hub 103, the sample is ejected from the needle. During an aspiration operation, the syringe plunger rod 111 is drawn away from the hub 103 so that a vacuum is created, and sample (air, gas, or a liquid) that is adjacent to the opening in the hub 103 is drawn into the syringe barrel 101.

The syringe plunger rod 111 has syringe plunger ribs 113 that extend radially from a center axis of the syringe plunger rod 111. While four ribs 113 are shown in the exemplary embodiment, other embodiments may include 1, 2, 3, 4 or more ribs. The cross-section of each plunger rib 113 in the present embodiment has a generally rectangular cross-section, although ribs with elliptical, oval, square or even semi-circular cross-sections may also be used, recognizing that an adapter Pi-support 126 will have a pair of legs that extend over opposite sides of the plunger rib 113.

Except for the syringe seal 107, which is made of rubber, such as synthetic rubber, the syringe parts are made from plastic, such as polypropylene for the barrel 101, and polyethene for the plunger rod 111. While the present embodiment uses parts made from plastic and synthetic rubber, other materials may be used as well, such glass and stainless steel barrels and/or plungers.

The syringe with adapter for single-handed aspiration operation 100 of FIG. 1 also includes a two-piece adapter. The adapter includes a first piece (120, 122, and 126) having an adapter extension spine 122 with an adapter forward flange 120 formed at a forward end thereof, and an adapter pi-support 126 formed at an opposite end. The pi-support 126 has this name since, as shown in FIG. 3c, the cross-section of the pi-support is substantially in the shape of the Greek letter "Pi", or Π. An adapter clip 124 is the second piece of the adapter and it removably clips about the syringe barrel 101 and at a top portion of the adapter clip 124 an upper opening that has passage which receives the adapter extension spine 122, which movably slides through the upper opening when a force is applied to the forward flange 120 or the thumb press 109. A back edge of the adapter clip 124 is prevented from being pushed off the end of the syringe barrel 101 by syringe lip and syringe flange.

Like the adapter clip 124, the adapter forward flange 120 clips about a forward portion of the syringe barrel 101 with legs that straddle at least 180 degrees (typically between 180 degrees to 270 degrees) of an outer surface of the syringe barrel 101. The adapter pi-support 126, which is disposed on the rear end of the adapter extension spine 122, itself has legs extending down from the adapter extension spine 122, where the legs have a gap formed there between that straddle one of the plunger ribs 113. A rear-surface of the adapter pi-support 126 also abuts the syringe thumb press 109.

The adapter forward flange 120, adapter extension spine 122, and adapter clip 124 may be made with various plastic materials such as polypropylene or polyethylene which have some flexibility to allow for clipping about various size barrels but still have relatively low coefficients of friction to allow relative ease in sliding over surfaces of the syringe barrel 101 and adapter clip 124. Moreover, the materials allow relative ease in sliding of forward flange 120 and adapter extension spine 122 over the outer surface of the syringe barrel 101 and inner surface of the adapter clip 124, respectively. The combination of a flexible material and partially open arcuate legs, which surround the syringe barrel between 190 degrees and 320 degrees (or another angle that is sufficient to allow for clipping over the syringe), allow for the adapter clip 124 (as well as the forward flange 120 which has a similar arcuate leg structure) to be mounted to the syringe barrel 101 by clipping action, as opposed to slipping the adapter clip 124 (or forward flange 120) over the hub 103 end of the syringe. However, rigid materials may be used as well such as stainless steel, acrylic, glass or other material that provides structural support and the ability to slide along a plastic surface. If the adapter clip 124, and/or forward flange 120 are made of rigid materials, they would be mounted to the syringe by being slid over the syringe hub 103 and around the syringe barrel 101.

The operator attaches the adapter clip 124 (second piece) to the first piece (forward flange 120, adapter extension spine 122, and pi-support 126 wedging a short side of the adapter extension spine 122 into a short side of the upper opening of the adapter clip 124, and then pressing a top surface of the extension spine 122 into the upper opening so the other short side of the adapter extension spine 122 snaps into the upper opening of the adapter clip 124. The adapter extension spine 122 is then held in place by at least two of its longer cross-sectional surfaces (upper surface and lower surface in FIG. 2 and FIG. 3b) being held by at least partial sides of the upper opening of the adapter clip 124. The adapter extension spine 122 will be slidably held in place as long as an inner surface of the upper opening extends past a widest part (in cross-section) of the extension spine 122.

As discussed above, the adapter clip 124 is either snapped about the syringe barrel 101 so the clip 124 is mounted on the syringe barrel 101 adjacent to the syringe lip 105, or the clip 124 is slid over the front end of the syringe barrel 101 until it engages the syringe lip 105. Likewise, the adapter's forward flange 120 is also clipped over the syringe barrel 101, or slid over the barrel 101 in the same way as the adapter clip 124. Once attached, the legs of the adapter's pi-support 126 are positioned to straddle the plunger rib 113 and also positioned so a rear face of the pi-support 126 abuts a surface of the plunger thumb press 109.

During an injection operation, the operator places the operators index and middle fingers over the forward surface of the barrel handle and places the operator's thumb on the plunger thumb press 109. The operator's index and middle fingers are placed directly on the barrel 101 so the finger do not contact the adapter extension spine 122, which will slide forward as a result of the force exerted by the operator on the plunger thumb press 109, which in turn pushes the pi-support 126/adapter extension spine 122/and forward flange 120 forward. Because there is only one extension spine 122 on the outside of the syringe barrel 101, the operator can easily perform the injection operation without having the operator's finger interfere with the movement of the extension spine 122.

During an aspiration operation, the operator keeps the adapter on the syringe, but repositions the operator's hand. In this case the operator places one or both index and middle fingers on the forward surface of the adapter's forward flange 120 and simultaneously places their thumb over the rear surface of the barrel handle. clamps the syringe barrel to the operator's palm with his thumb. As the operator applies rearward pressure to the front surface of the forward flange 120, the forward flange 120 slides rearward over the outer surface of the syringe barrel 101, while pushing the pi-support 126 against the plunger thumb press 109, thereby causing the plunger rod 111 and syringe seal 107 to move away from the syringe hub 103. During this aspiration operation, the forward flange 120, the extension spine 122, and the pi-support 126 all move rearward, while the adapter clip 124 remains in place and guides the extension spine 122 through the upper opening in the adapter clip 124.

In this way, the operator can perform an aspiration operation in a convenient and precise way, using only one hand. Furthermore, in contrast to a operator attempting to perform an aspiration operation with one hand using only a syringe, the operator can use a much greater dynamic range of the syringe without re-gripping. Moreover, with a standard syringe, using only one hand, the operator must grip the syringe barrel with the operator's palm, and then attempt to withdraw the plunger by exerting a force on an inner surface of the plunger thumb press 109 with the operator's thumb by extending the tip of the thumb away from the operator's palm. In contrast, the adapter of the present embodiment allows the operator to pull his fingers toward his palm when drawing the forward flange 120 rearward, thereby allowing for a longer movement of the plunger without needing to regrip the syringe.

Figure 2:
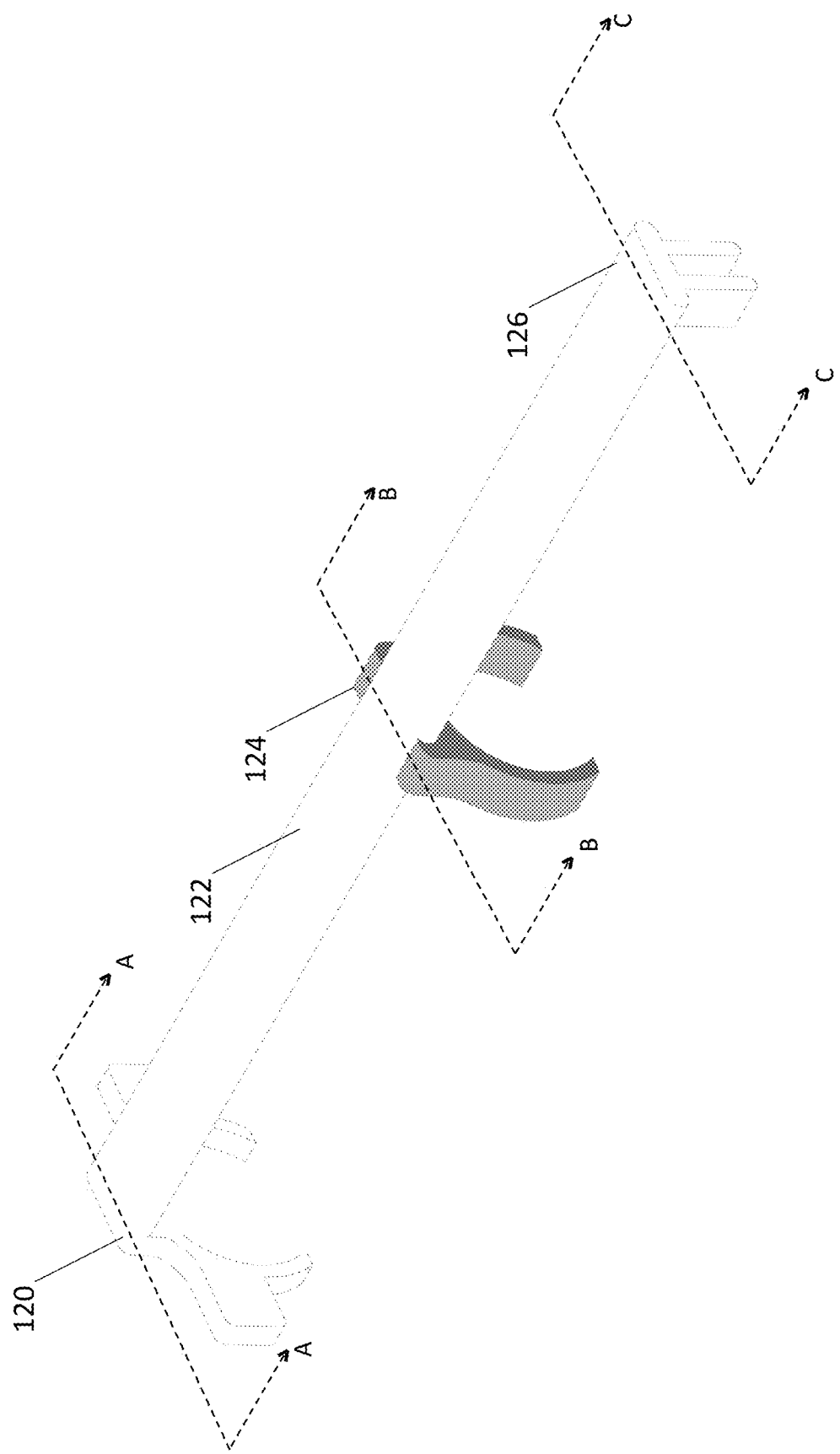
FIG. 2 is a perspective view of the adapter with sectional lines corresponding to the views shown in FIGS. 3a, 3b, and 3c.

FIG. 2 is a perspective view of the adapter with three cross-section cuts shown, corresponding to FIGS. 3a, 3b, and 3c. As can be seen from FIG. 2, the adapter forward flange 120 is integrally formed on one end of the adapter extension spine 122, and the pi-support 126 is formed on the opposite end. The adapter extension spine 122 is received in an upper opening of the adapter clip 124. As previously discussed, as the plunger rod 111 is moved in and out of the syringe barrel 101 during injection and aspiration operations, the extension spine 122 slides in the upper opening of the adapter clip 124, which remains fixed. Thus, the adapter clip 124 guides a precise movement of the extension spine 122 during one-handed operation.

FIG. 3a is a cross-section view of the "section a" in FIG. 2 and shows an outline of the shape of the forward flange 120. As seen, the forward flange 120 has opposing arcuate (or semi-arcuate) legs having lengths that extend at least 180 degrees about an outer surface of the syringe's barrel 101. Typically, the legs have a length that extend between 180 degrees to 270 degrees around the barrel 101, which allows for the forward flange 120 to be clipped about the syringe barrel 101, extending radially away from a center of the forward flange are finger-wings (shown in FIG. 3a next to element number 120) that provide surfaces on which a operator can apply backward pressure during an aspiration operation. At 90 degrees, there is a forward end of adaption extension spine 122.

FIG. 3b is a cross-section view of "section b" in FIG. 2 and shows an outline of the shape of the adapter clip 124. A first feature of the adapter clip 124 is similar arcuate (or semi-arcuate legs having lengths that extend at least 180 degrees about an outer surface of the syringe's barrel 101. Typically, the legs have a length that extend between 180 degrees to 270 degrees around the barrel 101 so as to hold the adapter clip 124 to the syringe barrel 101. The adapter clip 124 also includes the upper opening that has a complementary shape to, and receives, the extension spine 122 when snapped therein. As discussed above, the upper opening does not have complete inner walls on all sides. The upper opening at least has inner walls that extend around the widest (in cross-section) portion of the extension spine 122.

FIG. 3c is a cross-section view of "section c" in FIG. 2 and shows an outline of the pi-support 126. As seen, the pi support 126 is in the shape of the Greek symbol "Pi", or H, and includes two downward legs with a gap therebetween. A spacing of the gap is set to match a thickness of the plunger rib 113 (FIG. 1) so the plunger rib 113 is sandwiched between the legs.

Figure 4:
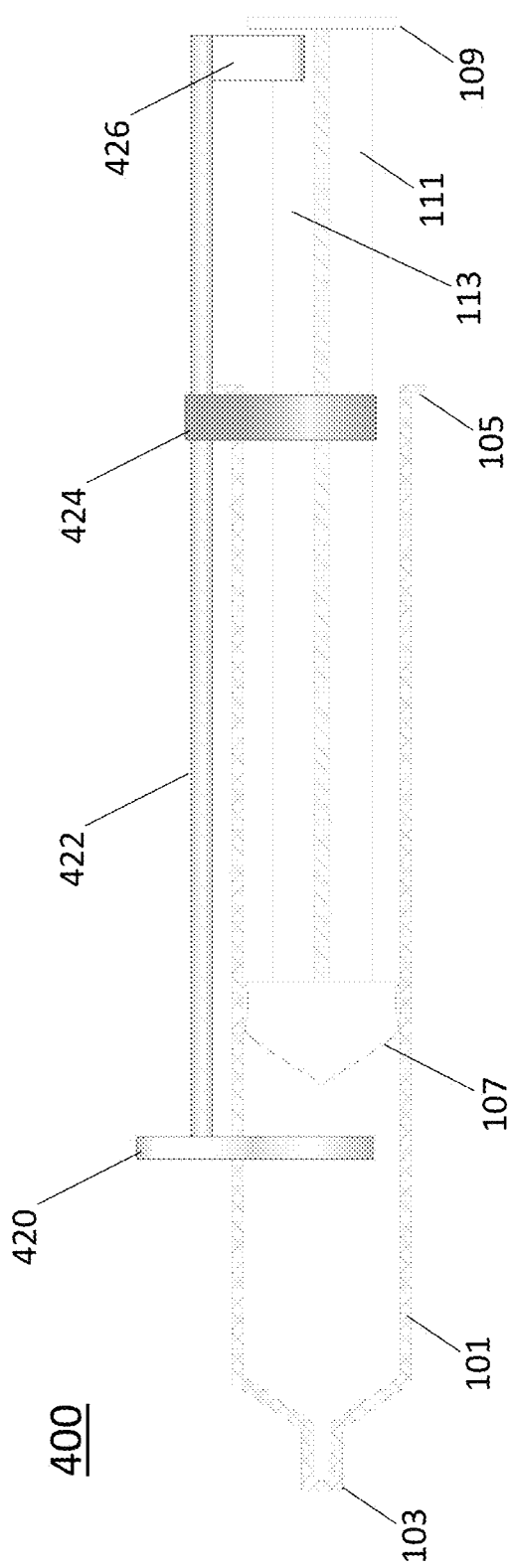
FIG. 4 is a side view of a syringe with an adapter for single-handed use of the syringe during an aspiration operation, according to a second embodiment.

FIG. 4 is a side view of a second embodiment of syringe with adapter for single-handed aspiration operation 400. The parts of the syringe are the same as the parts of the first embodiment, the extension spine 122/422, the adapter clip 124/424 and pi-support 126/426 are the same as the first embodiment so explanations of these components are provided above, or kept to a minimum in the present explanation. A shape of the forward flange 420 is different than that of the forward flange 120 of the first embodiment, as will be discussed with reference to FIGS. 5 and 6a.

Figure 5:
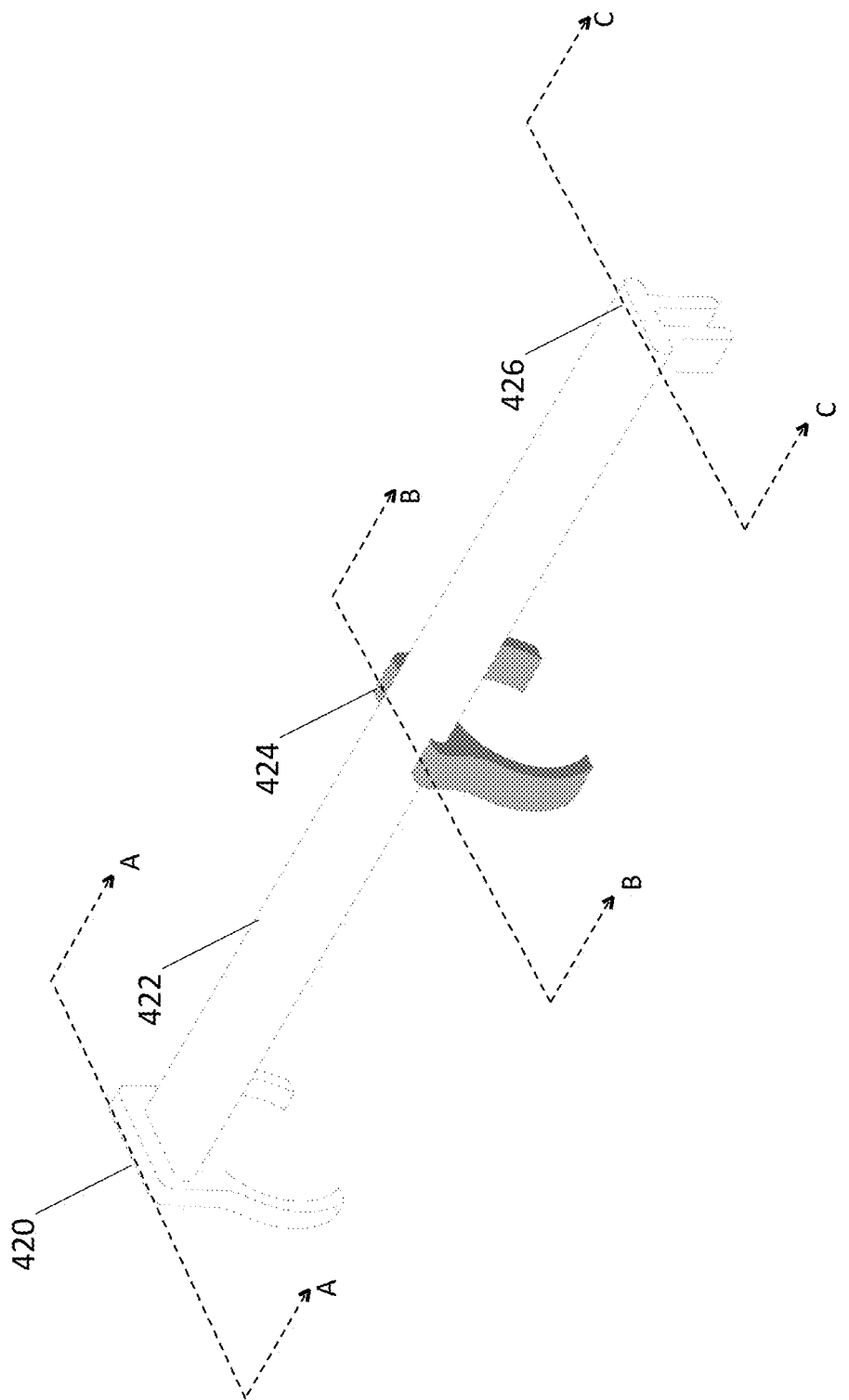
FIG. 5 is a perspective view of the adapter with sectional lines corresponding to the views shown in FIGS. 6a, 6b, and 6c.

As shown in FIG. 5 the adapter extension spine 422 includes the pi-support 426 on one end, and the forward flange 420 on the other end. An adapter clip 424 receives the extension spine 422 in its upper opening.

Figure 6A:
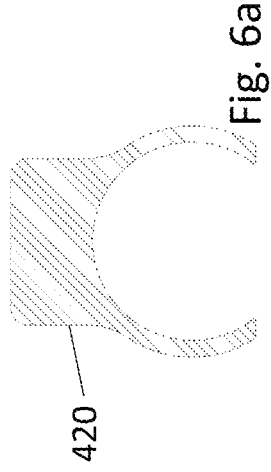
FIG. 6a is a cross-sectional view of an adapter forward flange according to the second embodiment.

FIG. 6a is a cross-section view of the "section a" in FIG. 5 and shows an outline of the shape of the forward flange 420. As seen, the forward flange 420 has opposing arcuate (or semi-arcuate) legs having lengths that extend at least 180 degrees about an outer surface of the syringe's barrel 101. Typically, the semi-arcuate legs have a length that extends between 180 degrees to 270 degrees around the barrel 101's outer surface, which allows for the forward flange 420 to be clipped about the syringe barrel 101, in addition to being slipped over the hub-end of the syringe during assembly. Extending radially away from a center of the forward flange is a single finger-wing that provides a sufficiently large surface for an operator to apply backward pressure using one or both of an index finger or middle finger during an aspiration operation.

Figure 6B:
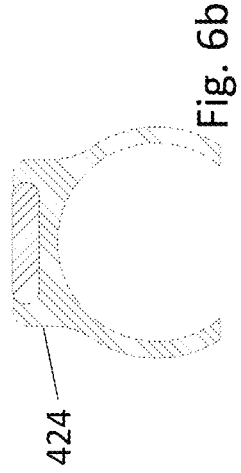
FIG. 6b is a cross-sectional view of an adapter clip according to the second embodiment.

FIG. 6b is a cross-section view of "section b" in FIG. 5 and shows an outline of the shape of the adapter clip 424, which is like that of 124 in FIG. 2.

Figure 6C:
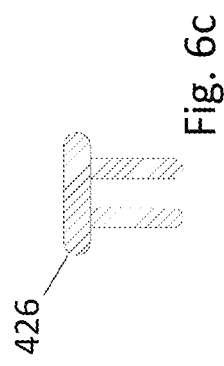
FIG. 6c is a cross-sectional view of an adapter pi-support according to the second embodiment.

FIG. 6c is a cross-section view of "section c" in FIG. 5 and shows an outline of the pi-support 426, like that of 126 of FIG. 2.

Figure 7:
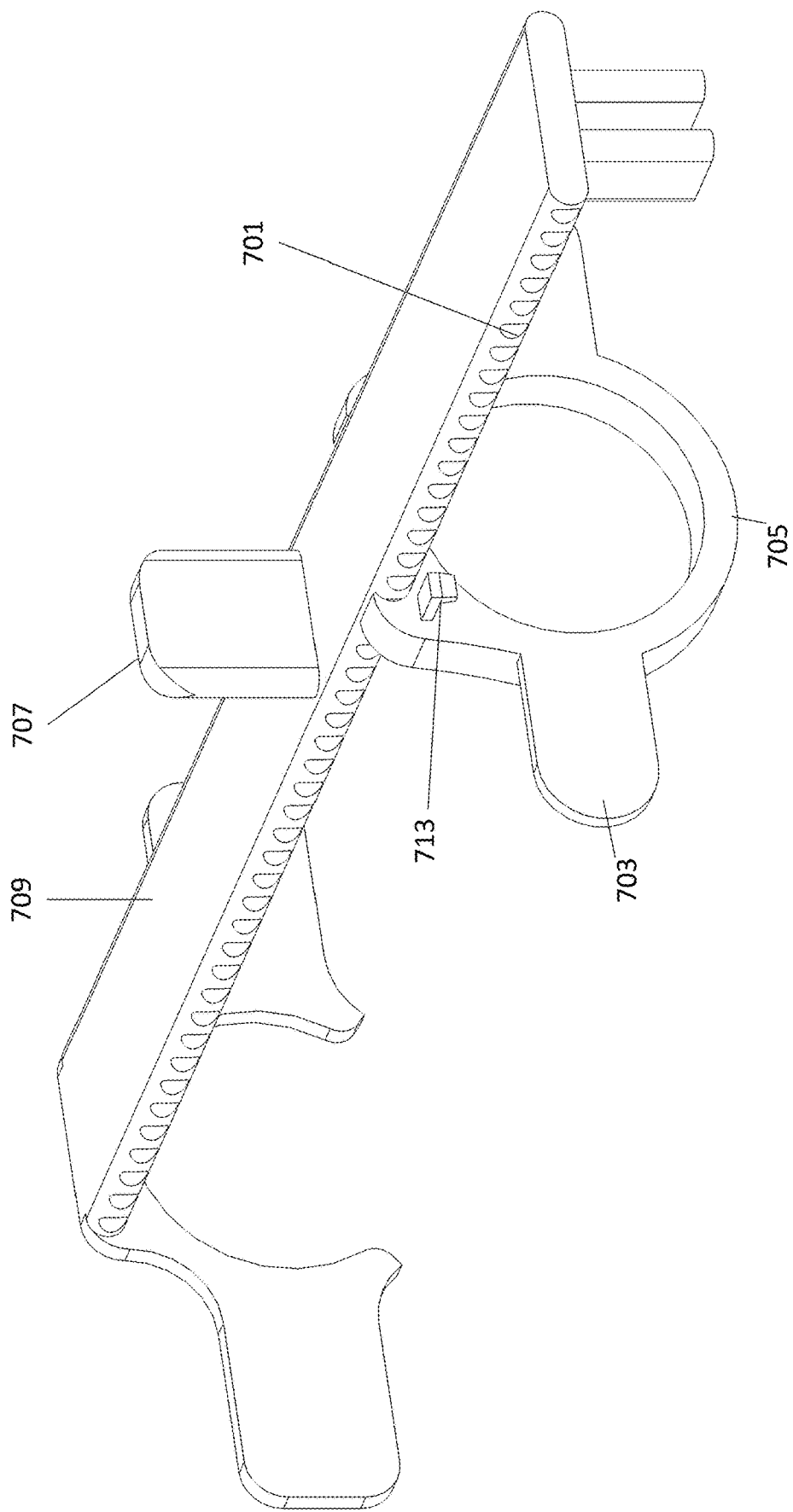
FIG. 7 is a perspective view of an adapter according to a third embodiment.

FIG. 7 is a perspective view of a third embodiment. FIGS. 8a and 8b are is a perspective view and cross-sectional view of a clip, respectively. A characteristic feature is the inclusion of pits 701 formed on the two edges of a ratcheted extension spine 709. The pits 701 are formed at predetermined spacings to correspond with a size and volume of sample held in the syringe. For example, the spacing between adjacent pits 701 may be set to correspond with 0.01 ml for a specific sized syringe. Thus, the spacing may be set to match size/volume of the syringe. Each pit 701 is a depression formed in the ratcheted extension spine 709 and positioned to receive a corresponding nub formed on nub wings 711 of the ring clip 705. Moreover, the nubs (protrusions) are formed on the inner surface of each nub wing 711 and each nub protrudes toward a corresponding pit 701 on the ratcheted extension spine 709. The ring clip 705 is made of plastic with sufficient flexibility that permits the clip ring to detachably attach to pairs of pits 701 on opposite sides of the ratcheted extension spine 709. To attach the ratcheted extension spine 709 to the ring clip 705, the operator holds the ratcheted extension spine 709 firm and urges the ratcheted extension spine 709 down toward the ring clip 705 so the nub wings 711 expand slightly so the nub wings 711 continue to move outward then inward and their respective nubs 711 snap into pits 701.

By including the pits, with associated nub in nub wing 711, the operator will receive a tactile indication of the amount of sample injected/aspirated. Moreover, while moving the ratcheted extension spine 709, the resilient force of the plastic nub wings 711 on the nubs increases as the nubs are forced out of the pits. The operator can feel this resilient force as an increased amount of effort to urge the movement of the ratcheted extension spine 709 relative to the syringe. The force increases while urging the nub on nub wing 711 out of a pit 701, and the force decreases as the nub on the nub wing 711 moves into a next pit 701. This change in force provides tactile feedback to the operator so the operator can carefully consider how much or how little sample is to be inserted or removed from the syringe. The clip has at rear surface a pair of hooks 713 that hold clip into the syringe lip 105 and keep it adherent to it, this will prevent spiral movement of the clip, and subsequently, the extension spine. The hook 713 has inner wall that matches at least the width of syringe lip 105. Moreover, once the operator slides clip ring 705 from the syringe hub 103 toward syringe lip 105 the hook 713 will slightly move upward then downward to clip around the syringe lip 105.

As shown in FIG. 8b, The clip ring 705 has a circular section, into which the barrel of a syringe is inserted. This embodiment is particularly well suited for thin, small syringes, such as 0.05 ml or 1 ml syringes. The clip ring 705 has clip flanges 703 that extend outward from the ring portion. These clip flanges 703 help to keep the ring clip 705 clip adherent to the cylinder handle during the injection process. During the injection process, the ring clip 705 will be moved until the clip flanges 703 abut the cylinder handle. The operator's forefingers will hold the clip flanges 703 while injecting. An accessory handle 707 is integrally formed over the outer surface of ratcheted extension spine 709, which serves as another push-surface for the operator to push against to urge a movement of the ratcheted extension spine 709 relative to the syringe during aspiration or injection when syringe size is larger than operator hand grip.

Various embodiments are described herein are brief summaries of selected embodiments are shown below.

(1) In a first embodiment, an adapter for single-handed operation of a syringe, the adapter includes
  a clip having a pair of arcuate legs that straddle at least half of an outer diameter of a barrel of a syringe, the clip having an upper opening; and
  an integrated structure including
  an extension spine that extends in an axial direction outside of the barrel of the syringe, the extension spine have a cross-sectional shape that matches at least a portion of an internal surface of the upper opening of the clip such that the extension spine is slidable within the upper opening of the clip,
  a forward flange disposed at a first end of the extension spine and having arcuate legs that straddle at least half of the outer diameter of the barrel of the syringe, and
  a support that is disposed on an opposite end of the extension spine and is positioned adjacent to a thumb press of a plunger rod of the syringe, wherein when a force is applied to the forward flange in a direction that the plunger is withdrawn from the barrel of the syringe, the force moves the extension spine through the upper opening of the clip and urges the support to move the thumb press of the plunger rod in an axial direction away from a hub of the syringe.

(2) The adapter of (1), wherein the support has at least one leg that extends away from the extension spine toward the plunger rod of the syringe, and a rear surface of the at least one leg is positioned against the thumb press of the plunger rod of the syringe.

(3) The adapter of (2), wherein the support includes another leg that extend away from the extension spine toward the plunger rod of the syringe such the at least one leg and the another leg form a pair of legs.

(4) The adapter of (3), wherein a cross-section of the support is substantially a Pi-shape with a gap between the pair of legs, a width of the gap is set to match a width of a rib on the plunger rod of the syringe, the pair of legs positioned to straddle the rib on the plunger rod of the syringe.

(5) The adapter of (1), wherein the pair of arcuate legs of the forward flange extend around the outer surface of the barrel of the syringe in an inclusive range of 180 degrees through 320 degrees.

(6) The adapter of (5), wherein the inclusive range is 180 degrees through 270 degrees.

(7) The adapter of (1), wherein the forward flange comprises plastic material.

(8) The adapter of (1), wherein the pair of arcuate legs of the forward flange form a closed ring and the forward flange is configured to slip over and fit around the barrel of the syringe.

(9). The adapter of (1), wherein the forward flange includes two finger-wings that extend radially away from a center of the forward flange.

(10) The adapter of (1), wherein the forward flange includes at least single finger-wing that extends radially away from a center of the forward flange.

(11) The adapter of (1), wherein the extension spine is a ratcheted extension spine, have a plurality of pits formed along an edge thereof, and the clip includes a nub wing having a nub that is configured to be received in a pit of the plurality of pits.

(12) The adapter of (1), wherein the extension spine has at most one accessory handle that extends away from center at its middle part and it has width of at most the edges of inner surface of upper opening of the clip.

(13) The adapter of (1) wherein the pair of arcuate legs of the clip extend around the outer surface of the barrel of the syringe in an inclusive range of 180 degrees through 320 degrees.

(14) The adapter of (13) wherein the inclusive range is 180 degrees through 270 degrees.

(15) The adapter of (13), wherein the arcuate legs of the clip are configured to clip around the outer surface of the barrel of the syringe.

(16) The adapter of (13), wherein the pair of arcuate legs of the clip form a closed circle and the clip is configured to slip over and fit around the barrel of the syringe.

(17) The adapter of (16), wherein the pair of arcuate legs of the clip have at least one flange adherent to barrel handle and extends radially away from a center of the clip.

(18) The adapter of (1) wherein the clip comprises plastic material.

(19) The adapter of (1), wherein the clip has pair of hooks at the rearward surface of the clip and have inner surface matches at least the width syringe lip.

(20) The adapter of (19), wherein the clip has at least one hook at its rearward surface.

(21) The adapter of (1), wherein the upper opening of the clip has inner walls that at least partially extend over a widest portion of a cross-section of the extension spine.

(22) A syringe assembly, is described that includes a syringe including a barrel having a hub formed at a front end, and a lip formed at a rear end, a plunger rod with a seal at one end that is inserted in the barrel, and a thumb press on an opposite end that is not in the barrel; and
   an adapter including
      a clip having a pair of arcuate legs that straddle at least half of an outer diameter of a barrel of a syringe, the clip having an upper opening, and
      an integrated structure including
         an extension spine that extends in an axial direction outside of the barrel of the syringe, the extension spine have a cross-sectional shape that matches at least a portion of an internal surface of the upper opening of the clip such that the extension spine is slidable within the upper opening of the clip,
         a forward flange disposed at a first end of the extension spine and having arcuate legs that straddle at least half of the outer diameter of the barrel of the syringe, and
         a support that is disposed on an opposite end of the extension spine and is positioned adjacent to a thumb press of a plunger rod of the syringe, wherein when a force is applied to the forward flange in a direction that the plunger is withdrawn from the barrel of the syringe, the force moves the extension spine through the upper opening of the clip and urges the support to move the thumb press of the plunger rod in an axial direction away from a hub of the syringe.

(23) The syringe assembly of (22), wherein the plunger rod comprises a rib, and the support has a cross-section that is substantially a Pi-shape with a gap between pair of legs that matches a width of the rib on the plunger rod, the pair of legs positioned to straddle the rib on the plunger rod of the syringe.

(24) The syringe assembly of (22), wherein the syringe comprises a lip, and the clip has a hook, the hook has a length that matches at least the width of the lip on the rear end of barrel, the hook positioned to hold the clip on the forward surface of barrel handle.

(25) The syringe assembly of (22), wherein the upper opening of the clip has inner walls that at least partially extend over a widest portion of a cross-section of the extension spine.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Obviously, numerous modifications and variations of the present invention are possible in light of the above teachings. It is therefore to be understood that within the scope of the appended claims, the invention may be practiced otherwise than as specifically described herein.

DRAWING ELEMENTS 100, 400: Syringe with adapter for single-handed aspiration operation
101: Syringe barrel
103: Syringe hub
105: Syringe lip
107: Syringe seal
109: Syringe plunger thumb press
111: Syringe plunger rod
113: Syringe plunger rib
120, 420: Adapter forward flange
122, 422: Adapter extension spine
124, 424: Adapter clip
126, 426: Adapter Pi-support
701: Pit
703: Clip flanges
705: Ring clip
707: Accessory handle
709: Ratcheted extension spine
711: Nub wing
713: Clip hook

The invention claimed is:
1. An adapter for single-handed operation of a syringe, the adapter comprising:
   a clip having a first pair of arcuate leas that straddle at least half of an outer diameter of a barrel of a syringe, the clip having an upper opening, and the syringe being operable independent of the adapter; and
   an integrated structure including
      an extension spine that extends in an axial direction along an outside of the barrel of the syringe, the extension spine have a cross-sectional shape that matches the upper opening of the clip, and is placed within the upper opening of the clip during assembly of the adapter on the syringe, and is slidable within the upper opening of the clip during an aspiration operation and an injection operation, a forward flange disposed at a first end of the extension spine and having a second pair of arcuate legs that straddle at least half of the outer diameter of the barrel of the syringe, the forward flange including a pair of finger-wings that extend in opposite directions radially away from a center of the forward flange, during assembly of the integrated structure with the syringe, the barrel of the syringe fitted within the second pair of arcuate legs, and a support that that is disposed on an opposite end of the extension spine and is positioned adjacent to a thumb press of a plunger rod of the syringe, wherein during the aspiration operation, in response to a force applied by fingers of an operator to respective forward surfaces of the finger-wings of the forward flange in a direction that the plunger is withdrawn from the barrel of the syringe, the force to the finger-wings moves the extension spine through the upper opening of the clip and urges the support to move the thumb press of the plunger rod in the axial direction away from a hub of the syringe, and during the injection operation, in response to a thumb of the operator pressed against the thumb press without the force applied to the finger-wings, the plunger rod is urged within the barrel of the syringe.

2. The adapter of claim 1, wherein
the support has a leg that extends away from the extension spine toward the plunger rod of the syringe, and a rear surface of at least one leg is positioned against a forward surface of the thumb press of the plunger rod of the syringe.

3. The adapter of claim 2, wherein
the support includes another leg that extends away from the extension spine toward the plunger rod of the syringe such the leg and another leg form a pair of legs.

4. The adapter of claim 3, wherein
a cross-section of the support is substantially a Pi-shape with a gap between the pair of legs, a width of the gap is set to match a width of a rib on the plunger rod of the syringe, the pair of legs positioned to straddle the rib on the plunger rod of the syringe.

5. The adapter of claim 1, wherein
the second pair of arcuate legs of the forward flange extend around the outer surface of the barrel of the syringe in an inclusive range of 180 degrees through 320 degrees.

6. The adapter of claim 5, wherein
the inclusive range is 180 degrees through 270 degrees.

7. The adapter of claim 1, wherein
the forward flange comprises plastic material.

8. The adapter of claim 1,
wherein the second pair of arcuate legs of the forward flange form a closed ring and the forward flange is configured to slip over and fit around the barrel of the syringe.

9. The adapter of claim 1,
wherein the extension spine is a ratcheted extension spine, have a plurality of pits formed along an edge thereof, and the clip includes a nub wing having a nub that is configured to be received in a pit of the plurality of pits.

10. The adapter of claim 1,
wherein the extension spine has an accessory handle that extends outward, away from a center portion of the extension spine.

11. The adapter of claim 1, wherein
the first pair of arcuate legs of the clip extend around the outer surface of the barrel of the syringe in an inclusive range of 180 degrees through 320 degrees.

12. The adapter of claim 11, wherein
the inclusive range is 180 degrees through 270 degrees.

13. The adapter of claim 11, wherein
the first arcuate legs of the clip are configured to clip around the outer surface of the barrel of the syringe.

14. The adapter of claim 1, wherein
the first pair of arcuate legs of the clip form a closed circle and the clip is configured to slip over and fit around the barrel of the syringe.

15. The adapter of claim 14, wherein
the first pair of arcuate legs of the clip have at least one flange adherent to a barrel handle and extend radially away from a center of the clip.

16. The adapter of claim 1, wherein
the clip comprises plastic material.

17. The adapter of claim 1, wherein
the clip has a pair of hooks in a rearward surface of the clip that are sized to match a lip of the syringe.

18. The adapter of claim 1, wherein
the clip has at least one hook at a rearward surface of the clip.

19. The adapter of claim 1, wherein
the upper opening of the clip has inner walls that at least partially extend over a widest portion of a cross-section of the extension spine.

20. A syringe assembly, comprising:
a syringe including
a barrel having a hub formed at a front end, and a lip formed at a rear end,
a plunger rod with a seal at one end that is inserted in the barrel, and a thumb press on an opposite end that is not in the barrel, the syringe being fully functional for aspiration and injection operations; and an adapter that is assembled on the syringe to allow for one-handed operation of the syringe in the aspiration and injection operations, the adapter including
a clip having a first pair of arcuate legs that straddle at least half of an outer diameter of a barrel of a syringe, the clip having a hook, the clip also having an upper opening, and
an integrated structure including
an extension spine that extends in an axial direction along an outside of the barrel of the syringe, the extension spine have a cross-sectional shape that matches the upper opening of the clip, and is placed within the upper opening of the clip during assembly of the adapter on the syringe, and is slidable within the upper opening of the clip during the aspiration operation and the injection operation,
a forward flange disposed at a first end of the extension spine and having a second pair of arcuate legs that straddle at least half of the outer diameter of the barrel of the syringe, the forward flange including a pair of finger-wings that extend in opposite directions radially away from a center of the forward flange, during assembly of the integrated structure with the syringe, the barrel of the syringe fitted within the second pair of arcuate legs, and a support that that is disposed on an opposite end of the extension spine and is positioned adjacent to the thumb press of the plunger rod of the syringe, wherein during the aspiration operation, in response to a force applied by fingers of an operator to respective forward surfaces of the finger-wings of the forward flange in a direction that the plunger is withdrawn from the barrel of the syringe, the force to the finger-wings moves the extension spine through the upper opening of the clip and urges the support to move the thumb press of the plunger rod in the axial direction away from the hub of the syringe, and during the injection operation, in response to a thumb of the operator pressed against the thumb press without the force applied to the finger-wings, the plunger rod is urged within the barrel of the syringe.

21. The syringe assembly of claim 20, wherein the plunger rod comprises a rib, and the support has a cross-section that is substantially a Pi-shape with a gap between a pair of legs, the gap is wider than the rib on the plunger rod, the pair of legs are positioned to straddle the rib on the plunger rod of the syringe.

22. The syringe assembly of claim 20, wherein the syringe barrel comprises a lip, and the hook of the clip has a length that matches at least a width of the lip on the rear end of barrel, the hook positioned to hold the clip on a forward surface of a barrel handle.

23. The syringe assembly of claim 20, wherein the upper opening of the clip has inner walls that at least partially extend over a widest portion of a cross-section of the extension spine.

\* \* \* \* \*